(12) United States Patent
Hartfield et al.

(10) Patent No.: US 8,759,765 B2
(45) Date of Patent: Jun. 24, 2014

(54) METHOD FOR PROCESSING SAMPLES HELD BY A NANOMANIPULATOR

(75) Inventors: Cheryl D. Hartfield, Dallas, TX (US); Thomas M. Moore, Dallas, TX (US); Brian P. Miller, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 13/567,487

(22) Filed: Aug. 6, 2012

(65) Prior Publication Data

US 2013/0037713 A1  Feb. 14, 2013

Related U.S. Application Data

(60) Provisional application No. 61/521,040, filed on Aug. 8, 2011.

(51) Int. Cl.
*G01N 23/00* (2006.01)
*G21K 7/00* (2006.01)

(52) U.S. Cl.
USPC ........... 250/311; 250/307; 250/309; 250/310; 250/440.11; 250/441.11; 378/86

(58) Field of Classification Search
USPC .............. 250/307, 309–311, 440.11, 442.11, 250/441.11; 378/86
See application file for complete search history.

(56) References Cited

U.S. PATENT DOCUMENTS

| | | | |
|---|---|---|---|
| 5,270,552 A | 12/1993 | Ohnishi et al. | |
| 6,420,722 B2 | 7/2002 | Moore et al. | |
| 6,570,170 B2 | 5/2003 | Moore | |
| 6,828,566 B2 | 12/2004 | Tomimatsu et al. | |
| 7,112,790 B1 | 9/2006 | Wang | |
| 7,659,506 B2 | 2/2010 | Avinun-Kalish et al. | |
| 2006/0113475 A1* | 6/2006 | Moore | 250/311 |
| 2008/0258056 A1 | 10/2008 | Zaykova-Feldman et al. | |

FOREIGN PATENT DOCUMENTS

| | | | | |
|---|---|---|---|---|
| JP | 2008122166 A | | 9/2004 | |
| JP | 2008-122166 | * | 5/2008 | ............... G01N 1/28 |
| JP | 2008122166 A | | 5/2008 | |
| JP | 11218473 A | | 4/2011 | |
| JP | 2012112770 A | | 6/2012 | |

OTHER PUBLICATIONS

International Preliminary Examining Authority, International Application No. PCT/US2012/49908, International Preliminary Report on Patentability, Aug. 23, 2013.
International Searching Authority, International Application No. PCT/US2012/049908l, International Search Report and the Written Opinion, Feb. 18, 2013.

* cited by examiner

*Primary Examiner* — Jack Berman
*Assistant Examiner* — Meenakshi Sahu
(74) *Attorney, Agent, or Firm* — John A. Thomas

(57) ABSTRACT

A method for processing a sample in a charged-particle beam microscope. A sample is collected from a substrate and the sample is attached to the tip of a nanomanipulator. The sample is optionally oriented to optimize further processing. The nanomanipulator tip is brought into contact with a stabilizing support to minimize drift or vibration of the sample. The attached sample is then stabilized and available for preparation and analysis.

13 Claims, 3 Drawing Sheets

METHOD FOR PROCESSING SAMPLES HELD BY A NANOMANIPULATOR

CLAIM FOR PRIORITY

This application claims the priority of U.S. Provisional Patent Application Ser. No. 61/521,040, filed Aug. 8, 2011, which application is incorporated by reference into the present application in its entirety.

BACKGROUND

1. Technical Field

This disclosure relates to methods and apparatus for processing and analyzing a microscopic sample, in particular, methods and apparatus for such processing and analyzing inside a charged-particle instrument such as a focused ion-beam microscope (FIB) or scanning electron microscope (SEM).

2. Background

FIB processes for lamella creation for transmission electron microscope (TEM) sample preparation have long been used in the semiconductor industry, including the use of nanomanipulators for FIB in situ lift-out (INLO) sample preparation, where the sample is lifted from some substrate, such as a semiconductor wafer. In addition to thin lamella, INLO samples have been adapted to other types of geometries such as wedges and micropillars, and they have been adapted to INLO-TEM types of in situ specimen analysis performed directly within the chamber of the charged-particle microscope. Examples of these analysis types include STEM, EDS, and EBSD, to name a few. The traditional INLO sample preparation is comprised of three main steps: 1) by induced-beam CVD deposition, glue, static, or other attachment means, attaching a nanomanipulator end-effector such as a fine probe tip to the sample destined for analysis, 2) while attached and supported by the end-effector, lifting the sample out or away from its original position, and 3) attaching the lifted sample to a new substrate or holder, such as a TEM grid, for completion of processing such as sample shaping by the ion beam or for inspection by various analytical means (such as the previously mentioned STEM, EDS, EBSD, or TEM analysis), performed either in situ or ex situ to the original charged-particle microscope chamber.

There are three primary reasons INLO samples are attached to a secondary support prior to further processing and analysis. First, this provides a means to easily manipulate a sample into different orientations to achieve the desired processing or analysis result based on using the degrees of freedom of the charged-particle beam microscope stage. Second, by placing the sample on a support directly connected to the microscope stage, additional drift or vibration effects outside those of the stage can be avoided. Third, the secondary holder or support provides an easy way to handle the sample for storage or when transferring the sample between different instruments.

The imaging requirements of charged-particle beam instruments are demanding, especially when imaging at the upper resolution limits in the range of angstroms to a few nm. Even the smallest vibration or drift can interfere with processing and analysis. In some cases, to achieve the desired performance, every unnecessary accessory on a charged-particle beam microscope is removed, as each accessory adds its own amount of drift and vibration to the entire chamber. Nanomanipulators, being accessories to these charged-particle beam instruments, have their own characteristic drift and vibration. These disturbances must be minimized to achieve the desired results if the processing and analysis are to occur while the sample is held by the end-effector of the nanomanipulator.

In practice, the sample is placed on a secondary support after the orientation steps are completed to provide stability against drift and vibration during processing, imaging and analysis. The lack of a solution to perform processing and analysis while on the end-effector means valuable instrument time is consumed with the third INLO step of attaching the lifted sample to a secondary support, such as a holder.

What is needed is a means to accomplish processing and analysis after the second lift-out step of attaching the lifted sample to the end-effector of the nanomanipulator without the need for attachment of the sample to a secondary holder.

DRAWINGS

DETAILED DESCRIPTION

This application uses the term "FIB" or "charged-particle beam instrument" generically for any kind of instrument using one or more radiation beams to assist chemical vapor-deposition procedures, etch, image or lift-out specimens in a vacuum. These terms as used here thus include instruments using ion beams, electron beams, other charged-particle beams, or light energy, such as a beam of laser light, or any combination of these beams. Unless otherwise stated, the terms "end-effector", "probe tip" or "tip" refer to any part of a manipulator apparatus intended to be attached to a specimen for lift-out or manipulation and are equivalent in this disclosure. A suitable nanomanipulator system is the AutoProbe® 300, manufactured by Omniprobe, Inc. of Dallas, Tex. In the Omniprobe apparatus, the end-effector is typically a fine tungsten needle probe tip.

A solution to the requirement for reduced drift and vibration is provided by moving the end-effector holding the lifted sample until it touches a support structure that is fixed to the microscope stage (100), and continuing to move the end effector against the support until a sufficient pushing force is obtained, where no discernible vibration is observed. With this method, no vibration is observed even at magnifications of up to 400,000 times, and accurate processing and analysis can be performed while the sample is held on the tip.

Figure 3:
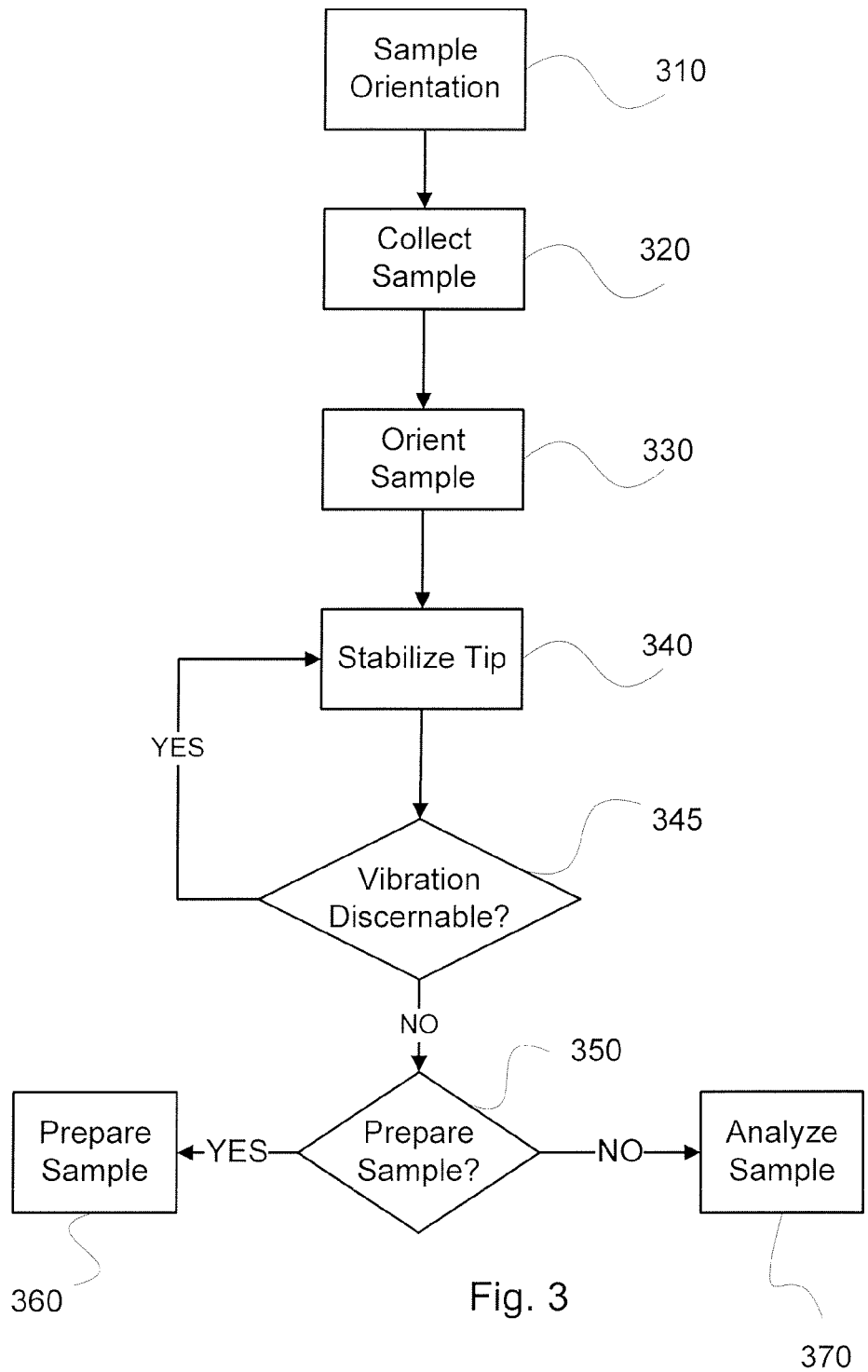
FIG. 3 is a flow chart showing the method.

The flow chart in FIG. 3 shows the steps of the method. The method may start optionally with the step 310 of Pre-Collection Sample Orientation. Before collection of the sample (120) from the substrate (not shown) with the nanomanipulator tip (110), the support, such as the microscope stage (100) supporting the substrate, can be positioned so that after the sample (120) has been collected by the nanomanipulator tip (110), the position of the sample (120) on the nanomanipulator tip (110) is optimized for subsequent processing, or is suitable for final orientation using the nanomanipulator after sample (120) collection.

In step 320, the Collect Sample step of the process, the sample (120) is collected from the substrate by attaching the sample (120) to the nanomanipulator tip (110). This attachment can be made, for example, with static electric attraction, an adhesive material, mechanical gripping, or by material deposition using charged-particle beam assisted material deposition with a chemical vapor, or charged-particle beam induced redeposition from a neighboring solid material. The means of attachment are not limited to the above examples. Once collected, the nanomanipulator can be used to translate the sample (120) to a suitable location for later orientation and preparation.

At step 330, the sample (120) may optionally be oriented. After the sample (120) has been collected onto the nanomanipulator tip (110), the nanomanipulator tip (110) can be positioned to optimize subsequent processing using the nanomanipulator's X, Y and Z orthogonal axes, rotation about the nanomanipulator tip (110) axis, and pitch (tilt) of the nanomanipulator tip (110) about a pitch axis that is perpendicular to the nanomanipulator tip (110) axis.

Figure 1:
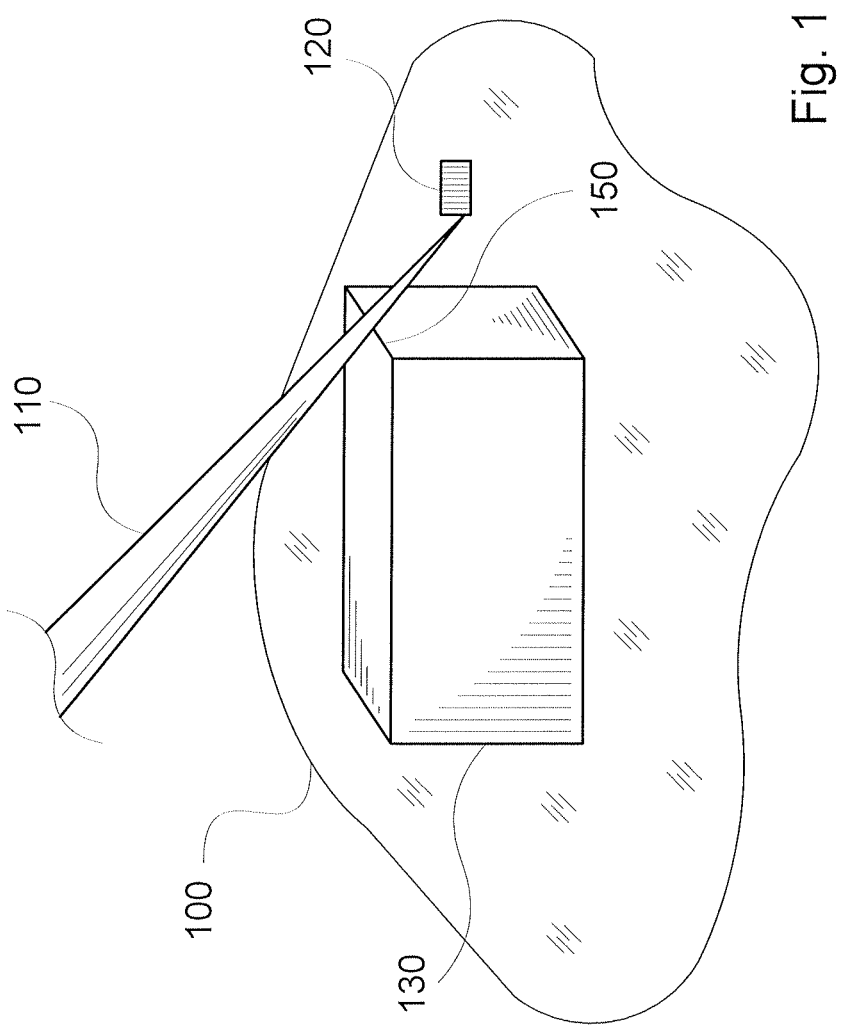
FIG. 1 shows an exemplary embodiment of the method for collecting, processing and analyzing a sample (120) while it is held by the end effector or tip (110) of a nanomanipulator, where the end-effector (110) is contacting the straight edge (150) of a stabilizing support (130) mounted on the microscope stage (100).
Figure 2:
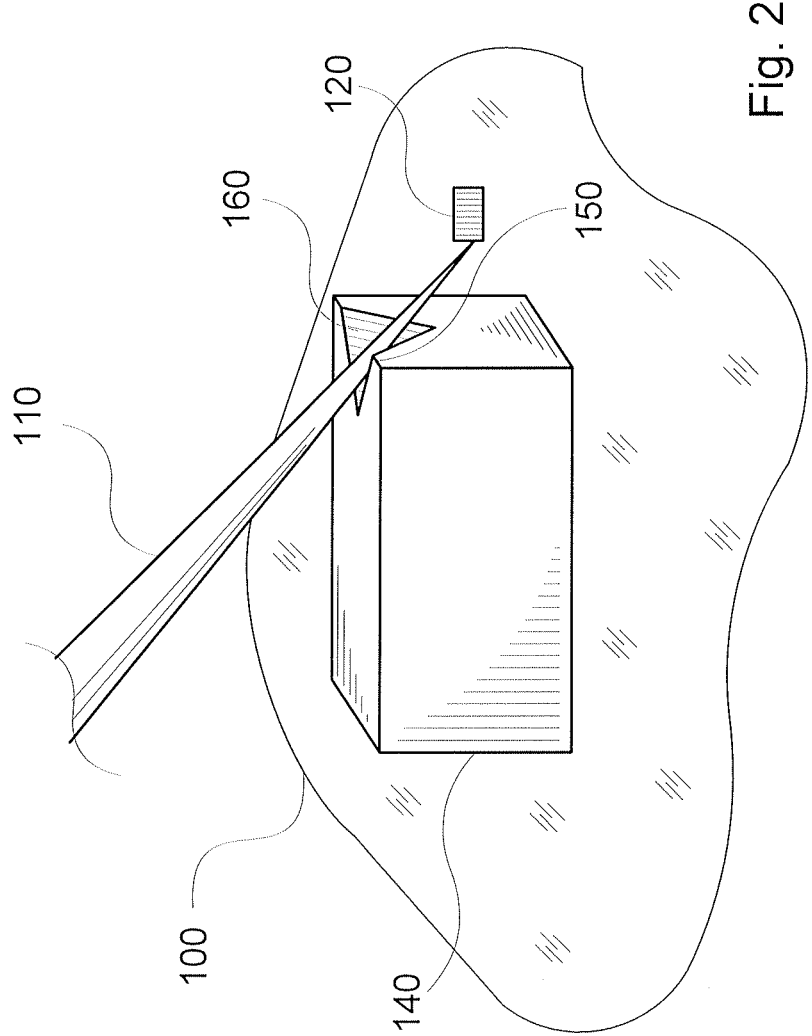
FIG. 2 shows an additional exemplary embodiment of the method for collecting, processing and analyzing a sample (120) while it is held by the end effector (110) of a nanomanipulator, where the end-effector (110) is contacting a V groove (160) created in the straight edge (150) of a stabilizing support (130) mounted on the microscope stage (100).

At step 340, the tip is stabilized. FIGS. 1-3 show the process. After the sample (120) has been collected, and optionally the orientation of the sample (120) on the nanomanipulator tip (110) has been optimized, the nanomanipulator tip (110) can be mechanically stabilized by bringing the nanomanipulator tip (110) into physical contact with a stabilizing support (130). This can be accomplished by translating the nanomanipulator tip (110) to the stabilizing support (130), moving the stabilizing support (130) to make contact with the nanomanipulator tip (110) or a combination of both movements. At step 345, the sample (120) is viewed to determine if any vibration of the sample (120) is discernible. If so, control returns to step 340 to continue to move the nanomanipulator tip (110) against the support (130); if not, then the sample (120) is ready to be prepared at step 350. The stabilizing support (130) can be a passive straight edge (150), or, in another embodiment (140), a passive straight edge with a V notch (160) as shown in FIG. 2, or a more complicated shape designed to passively minimize vibration and drift of the sample relative to the charged-particle beam, including shapes that mechanically capture the nanomanipulator tip (110). Also, the stabilizing support (130) can provide active drift or vibration minimization using feedback control from the charged-particle beam image or from a sensor or sensors attached to the nanomanipulator, to the sample stage (100) or to the charged-particle beam microscope.

At step 350 a decision is made to either prepare the sample (120) or analyze it at that time. The sample preparation (step 360) can include changing the sample (120) shape or changing the sample (120) properties, such as by annealing the sample (120) using heat. The particle beam can be used to reshape the sample (120) to optimize it for subsequent analysis. The reshaping can include elimination of material by ion beam milling, for example. The reshaping might also include adding material with charged-particle beam assisted deposition, for example, if a particular shape is required for subsequent analysis.

In step 370, the sample (120) is analyzed. Once prepared, the sample (120) can be analyzed immediately in the charged-particle beam microscope, such as with scanning transmission electron microscopy (STEM) or energy dispersive X-ray analysis (EDS), or the sample (120) can be removed and taken to a separate instrument for analysis, such as to a transmission electron microscope (TEM).

None of the description in this application should be read as implying that any particular element, step, or function is an essential element which must be included in the claim scope; the scope of patented subject matter is defined only by the allowed claims. Moreover, none of these claims are intended to invoke paragraph six of 35 U.S.C. Section 112 unless the exact words "means for" are used, followed by a gerund. The claims as filed are intended to be as comprehensive as possible, and no subject matter is intentionally relinquished, dedicated, or abandoned.

We claim:

1. A method for processing a sample held by a nanomanipulator tip comprising:
    bringing the nanomanipulator tip into contact with a stabilizing support; and,
    stabilizing the sample using feedback control;
    where stabilizing the sample using feedback control further comprises:
        continuing to move the nanomanipulator tip against the stabilizing support until substantially no discernible vibration of the sample is observable.

2. The method of claim 1 further comprising orienting the sample to optimize further processing.

3. The method of claim 1 further comprising preparing the stabilized sample for analysis.

4. The method of claim 1 further comprising analyzing the stabilized sample.

5. The method of claim 1, where bringing the nanomanipulator tip into contact with the stabilizing support further comprises translating the nanomanipulator tip to contact the stabilizing support.

6. The method of claim 1, where bringing the nanomanipulator tip into contact with the stabilizing support further comprises translating the stabilizing support to contact the nanomanipulator tip.

7. The method of claim 3 where preparing the sample further comprises ion-beam milling to shape the sample.

8. The method of claim 4 where analyzing the sample further comprises scanning transmission electron microscopy of the sample.

9. The method of claim 4 where analyzing the sample further comprises energy dispersive X-ray analysis of the sample.

10. A method for processing a sample in a charged-particle beam microscope, the method comprising:
    collecting the sample from a substrate;
    attaching the sample to a nanomanipulator tip;
    orienting the sample to optimize further processing;
    bringing the nanomanipulator tip into contact with a stabilizing support;
    stabilizing the sample using feedback control;
    where stabilizing the sample using feedback control further comprises:
    continuing to move the nanomanipulator tip against the stabilizing support until substantially no discernible vibration of the sample is observable;
    preparing the sample for analysis; and,
    analyzing the sample.

11. The method of claim 10 where preparing the sample further comprises ion-beam milling to shape the sample.

12. The method of claim 10 where analyzing the sample further comprises scanning transmission electron microscopy of the sample.

13. The method of claim 10 where analyzing the sample further comprises energy dispersive X-ray analysis of the sample.

\* \* \* \* \*